United States Patent [19]

Sramek

[11] Patent Number: 5,503,157
[45] Date of Patent: Apr. 2, 1996

[54] SYSTEM FOR DETECTION OF ELECTRICAL BIOIMPEDANCE SIGNALS

[76] Inventor: Bohumir Sramek, 19211 Edgehill Dr., Irvine, Calif. 92715

[21] Appl. No.: 405,841

[22] Filed: Mar. 17, 1995

[51] Int. Cl.⁶ .......................................................... A61B 5/02
[52] U.S. Cl. .......................................... 128/693; 128/734
[58] Field of Search ..................................... 128/691, 692, 128/693, 734

[56] References Cited

U.S. PATENT DOCUMENTS

| | | |
|---|---|---|
| 4,450,527 | 5/1984 | Sramek . |
| 4,807,638 | 2/1989 | Sramek . |
| 4,836,214 | 6/1989 | Sramek . |
| 4,870,578 | 9/1989 | Vysin et al. . |
| 4,953,556 | 9/1990 | Evans ........................................ 128/693 |
| 5,309,917 | 5/1994 | Wang et al. ............................. 128/734 |
| 5,385,576 | 1/1995 | Noren et al. ............................ 128/693 |
| 5,423,326 | 6/1995 | Wang et al. ............................. 128/734 |

*Primary Examiner*—Angela D. Sykes
*Assistant Examiner*—Eric F. Winakur
*Attorney, Agent, or Firm*—David A. Farah; Michael Zarrabian; Sheldon & Mak, Inc.

[57] ABSTRACT

A system and method for detection of electrical bioimpedance signals in a human or animal body segment. The system comprises a constant current generator for generating a periodic high frequency current output across a body segment in response to a periodic control input signal, a controller for generating a periodic control output signal to control operation of the current generator and an electrical bioimpedance detector for detecting a voltage generated across the body segment by the flow of current in the segment. The electrical bioimpedance detector generates an output signal indicative of bioimpedance in the body segment. The periodic generation of a current across a body segment alleviates the potentially detrimental effects of a continuous current on body segment tissue and reduces interference with the function of certain pacemakers.

16 Claims, 6 Drawing Sheets

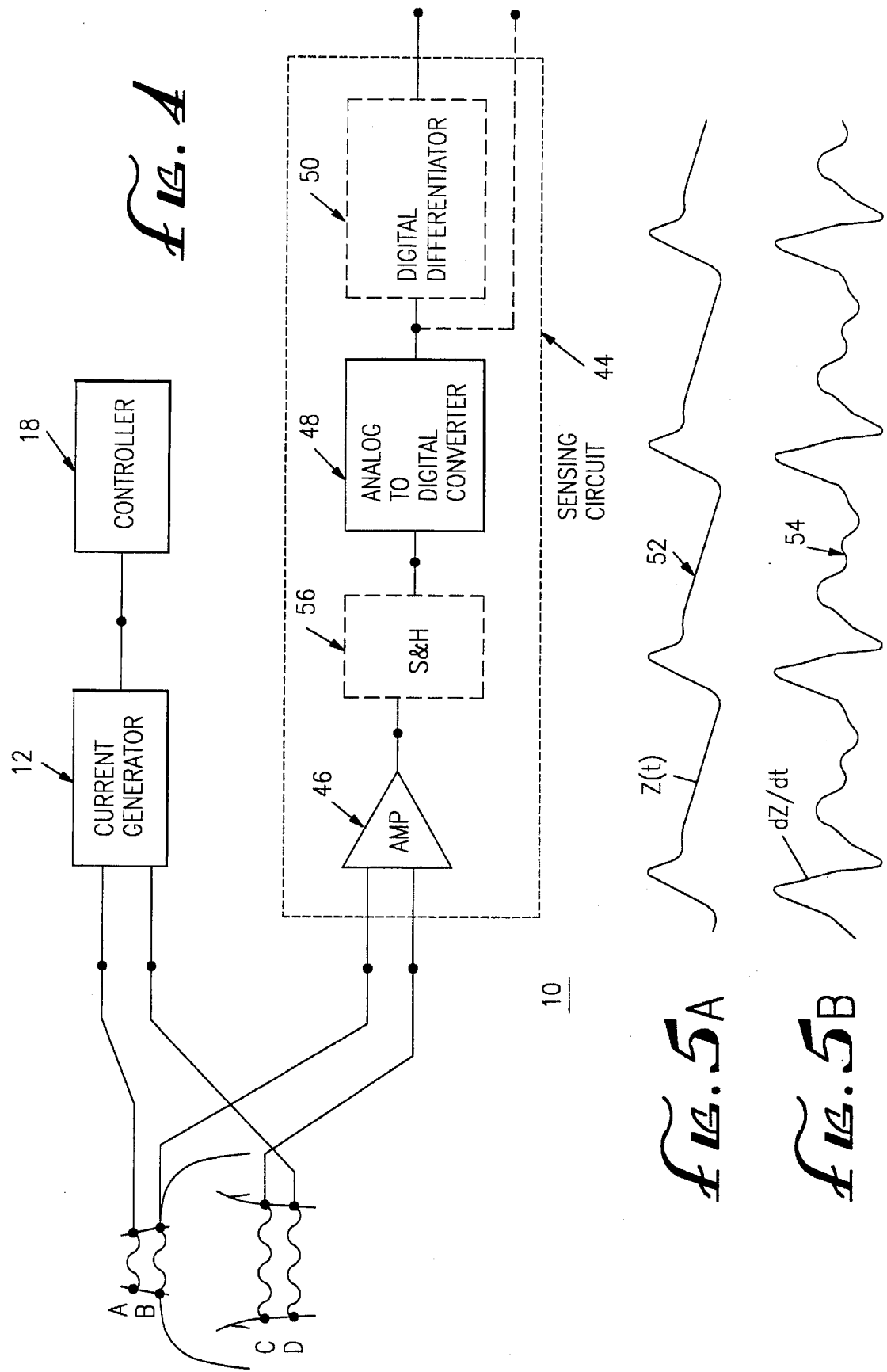

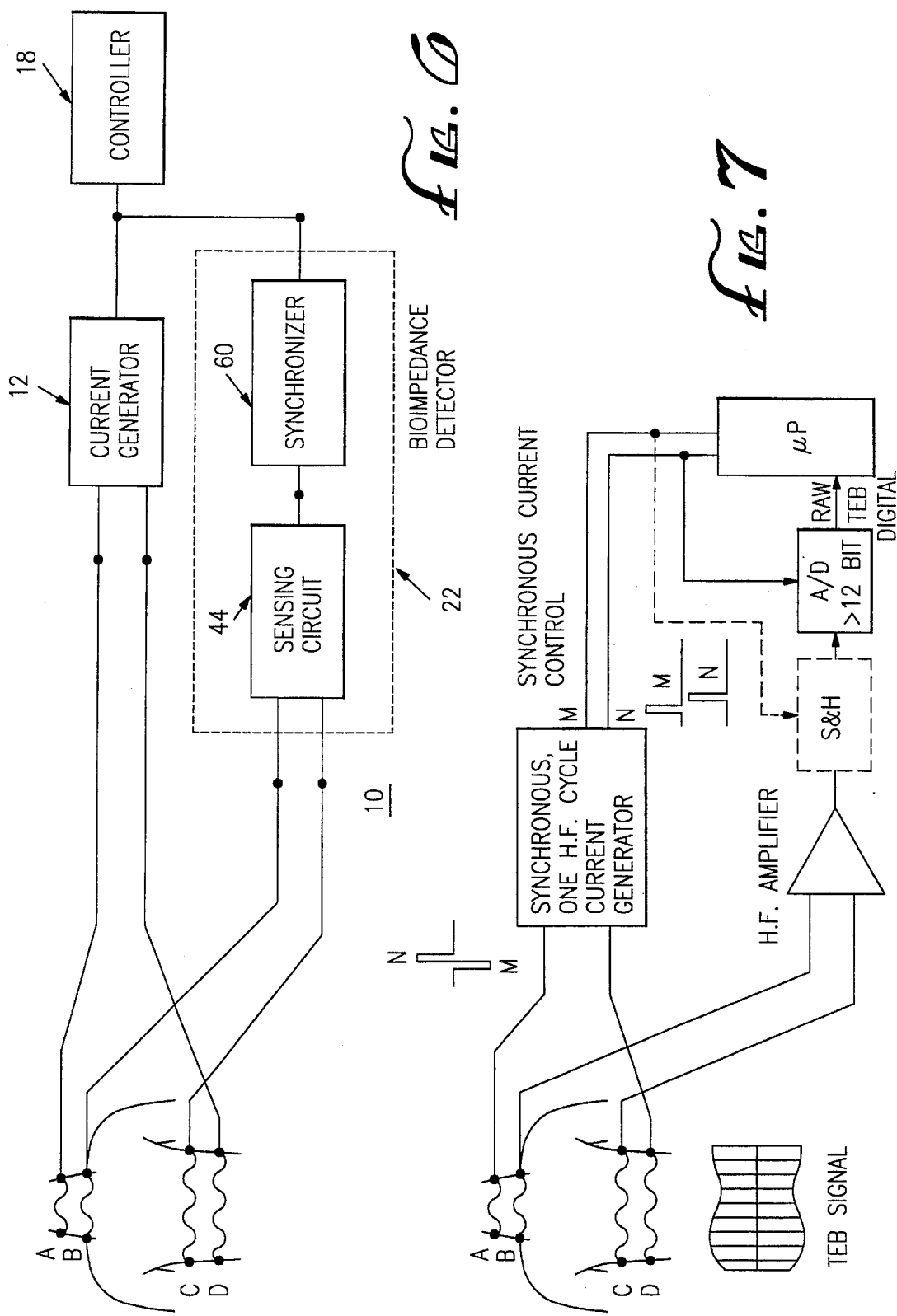

SYSTEM FOR DETECTION OF ELECTRICAL BIOIMPEDANCE SIGNALS

BACKGROUND

Disorders affecting the cardiovascular system are major causes of morbidity and mortality in all developed countries. Treating these diseases accounts for a significant portion of health care resources. Further, temporary and permanent disabilities secondary to these diseases have substantial effects on the economic productivity of developed countries.

Accurate diagnosis and efficacious treatment of diseases affecting the cardiovascular system depend in large part on determining several parameters of cardiac function and on determining the blood flow to various tissues. The global blood flow is cardiac output. One useful way of determining regional or global blood flow is by measuring electrical bioimpedance in a body segment, including superficial organs. In the thorax, cardiac output is measured.

The electrical bioimpedance of a body segment depends upon a number of factors including the volume of blood or volume of fluid in the segment and the changes of electrical conductivity of the body segment. Several parameters of cardiac function and the hemoperfusion of the various tissues can be determined by measuring the magnitude of components of bioimpedance which are unchanging, and the rate and amplitude of changes in components of bioimpedance caused by arterial distension and blood flow.

Existing bioimpedance measuring systems utilize a continuous current generator to generate a continuous, constant magnitude measurement current through a human or animal body segment. Impedance to the continuous current flow in the body segment generates a voltage difference across the body segment. The amplitude of the voltage is modulated by changes in body segment electrical conductivity caused by changes in blood volume and velocity in the body segment which becomes an impedance transducer. The voltage across the transducer is measured by a bioimpedance detector, and the detector generates an output signal indicative of the impedance in the body segment.

The continuous, constant magnitude, measurement current used in existing systems has a magnitude ranging between 1 mA and 4 mA Root Mean Square (RMS). The signal frequency of the current used is between 20 kHz (one cycle period of 50 μsec) to 100 kHz (period of 10 μ sec).

While functional, existing bioimpedance measuring systems are associated with some disadvantages. First, as stated above, existing systems utilize a continuous, constant magnitude, measurement current. This current is in a high frequency range and is delivered to living tissue for a protracted time. Though not definitively proven, high frequency current may be detrimental to living tissues including tissues present in the thorax.

Further, although the measurement current flows through the body segment continuously, the bioimpedance detectors utilized in existing systems sample the measurement current only 200 to 400 times a second (i.e. every 5 to 2.5 msec). Therefore, detrimental high frequency currents unnecessarily flow through the body segment between sampling.

A second disadvantage of existing systems is that the bioimpedance detectors utilized in such systems require several consecutive levels of amplifier circuits. Each amplifier circuit undesirably amplifies the input noise from signals detected in a body segment, thereby necessitating an increase in the magnitude of the measurement current to maintain an suitable signal to noise ratio. Multiple amplifier circuits require substantial area on printed circuit boards and utilize numerous circuit components thereby increasing the cost and power consumption of the system. The complexity of multiple amplifier systems decreases the reliability of the systems and increases the frequency of required maintenance.

A further disadvantage of existing systems is that the continuous, constant magnitude, measurement current they use can interfere with the operation of rate-responsive devices such as pacemakers.

Generally, the magnitude of the measurement current needed in bioimpedance measuring systems is determined by the level of noise in electronic circuitry in the bioimpedance detector. Reducing the magnitude of the measurement current also reduces the signal to noise ratio thereby decreasing the sensitivity of the system.

Therefore, it would be advantageous to have an electrical bioimpedance detection system that reduces exposure of a body segment to the measurement current without reducing the magnitude of the measurement current. Further, it would be advantageous to have an electrical bioimpedance detection system which does not expose the body segment to a continuous, high frequency measurement current. Still further, it would be advantageous to have an electrical bioimpedance detection system which does not interfere with rate-responsive devices such as pacemakers. Also, it would be advantageous to have an electrical bioimpedance detection system which would eliminate the need for multiple amplification circuits.

SUMMARY

The present invention satisfies these needs. According to one aspect of the present invention, there is provided a system for determining bioimpedance in a human or animal body segment. The system comprises a current generator for generating a periodic high frequency current output across the body segment in response to a periodic control input signal, a controller for generating a periodic control output signal to control operation of the current generator and an electrical bioimpedance detector for detecting a voltage generated across the body segment by the flow of current in the segment. The detector generates an output signal indicative of impedance in the body segment.

Preferably, the bioimpedance detector comprises a sensing circuit for receiving said voltage and generating an output signal having a magnitude that changes in accordance with the content or flow of fluid in the animal's body between the first and the second portions. The sensing circuit comprises an amplifier for receiving and amplifying said voltage, and an analog-to-digital converter responsive to the amplifier, for converting the signal to a digital output signal representative of impedance in the body segment.

The sensing circuit can further comprise a digital differentiator responsive to the analog-to-digital converter. The differentiator generates data representing a differentiated voltage output signal having a magnitude proportional to the rate of change of electrical bioimpedance in the body segment.

In another embodiment of the invention, the bioimpedance detector comprises a third input terminal electrically connected to the output terminal of the controller, whereby the output signal of the controller is simultaneously received by both the current generator and the bioimpedance detector. The bioimpedance detector further comprises a synchronizer coupled to the sensing circuit, for controlling the operation of the sensing circuit in response to a control signal from the controller. The sensing circuit periodically detects the voltage in synchrony with the operation of the current generator. Preferably, the synchronizer comprises an electrically controlled switch responsive to control signals from the controller. In this embodiment, the analog-to-digital convertor is responsive to the periodic control signal of the controller to periodically convert the output signal of the amplifier to a digital up signal representative of impedance in the body segment.

The present invention also provides a method of determining or measuring fluid content or fluid flow in a human or animal body comprising periodically generating a high frequency current, applying the current to a first and a second portion of the body, detecting a voltage between the first and the second portion of the body caused by impedance to the current flow in the body between the first and the second portions, and generating a signal based on the detected voltage. The signal is indicative of impedance in the body between the first and the second portions. Preferably, the step of detecting comprises periodically detecting said voltage in synchrony with the periodic generation of the current.

DRAWINGS

These and other features, aspects and advantages of the present invention will become understood with reference to the following description, appended claims and accompanying drawings where:

FIG. 4 is a block diagram illustrating the components of a system for measuring bioimpedance, according to another aspect of the present invention, connected to a human or animal body;

FIG. 5a is a graph of a voltage wave form generated by the amplifier portion of a system for measuring bioimpedance, according to one aspect of the present invention;

FIG. 5b is a graph of the differentiated wave form of the graph of FIG. 5a, generated by a digital differentiator portion of a system for measuring bioimpedance, according to one aspect of the present invention;

FIG. 6 is a block diagram of a system for measuring bioimpedance, according to one aspect of the present invention, where operation of the current generator portion and the bioimpedance detector portion are synchronized by a controller portion;

FIG. 7 is a block diagram illustrating an example embodiment of a system for measuring bioimpedance, according to one aspect of the present invention, connected to a human body.

DESCRIPTION

Figure 1:
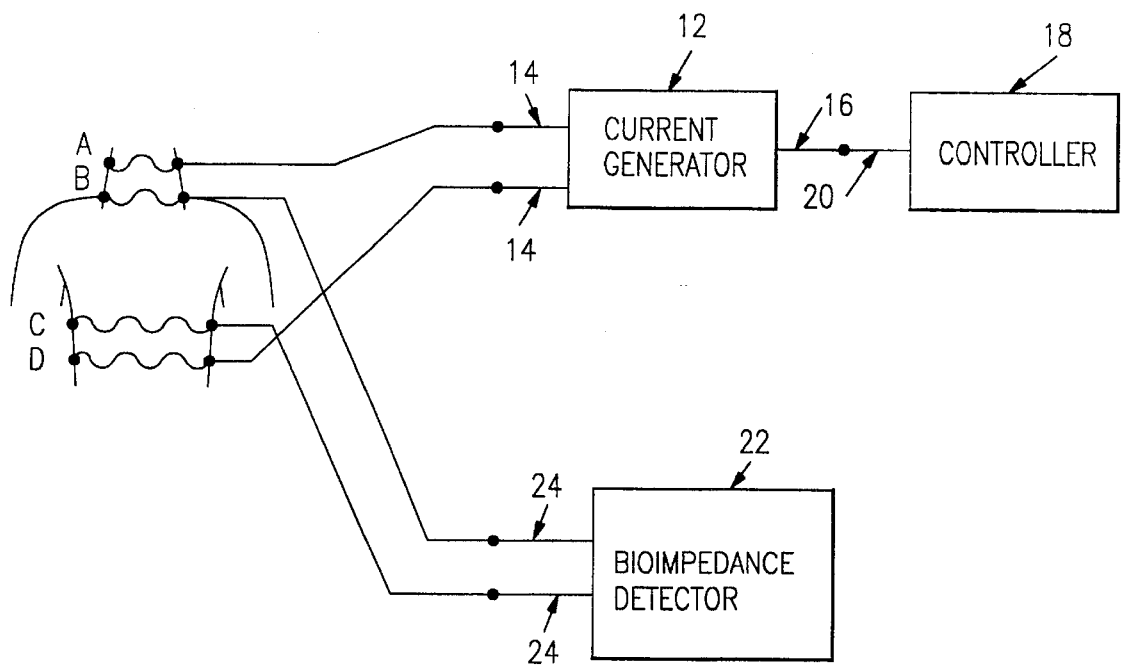
FIG. 1 is a block diagram illustrating the components of a system for measuring bioimpedance, according to one aspect of the present invention, connected to a human or animal body.

Referring now to FIG. 1, there is illustrated a diagram of a system 10 for determining or measuring fluid content or fluid flow such as blood flow, in a human or animal body segment according to one aspect of the present invention. The system 10 comprises a current generator 12 for generating a periodic high frequency current output in response to a periodic control input signal. The current generator 12 comprises a first and a second output terminal 14 for carrying the current output. The output terminals 14 are electrically connectable to a first and a second portion of a human body. The current generator 12 further includes an input terminal 16 for receiving the control input signal.

The system 10 further comprises a controller 18 for generating a periodic control output signal to control operation of the current generator 12. The controller includes an output terminal 20 for carrying the control output signal. The output terminal 20 is electrically connected to the input terminal of the current generator.

The system further comprises an electrical bioimpedance detector 22 for detecting a voltage signal between the first and the second body portions caused by flow of current between the two body portions. The detector 22 generates an output signal indicative of impedance between the first and the second portions, in response to the voltage signal. The bioimpedance detector comprises a first and a second input terminal 24 for detecting the voltage signal, and an output terminal for carrying the detector's output signal. The first and the second input terminals 24 are electrically connectable to the body proximate of the first and second output terminals 14, respectively.

The current generator further comprises an electrically controlled switch 26 coupled to the current source 28, for regulating the operation of the current source 28 in response to a periodic control signal. The periodic control signal causes the switch 26 to open and close periodically. The current source generates a current output only when the switch is closed. Therefore, the current generator advantageously generates a periodic current output across a body segment instead of a continuous constant magnitude current avoiding problems associated with existing systems, as discussed herein.

The output terminals of the current generator are typically current injecting electrodes, shown in FIG. 1 as a pair of spot electrodes. The voltage signal generated in the body between the first and the second portions, is proportional to the magnitude of the periodic current and also proportional to the electrical bioimpedance of the tissue between the two current injecting electrodes. The voltage signal is detected by the input terminals 24 of the bioimpedance detector, wherein the input terminals comprise a pair of voltage sensing electrodes located on the body between the two current injecting electrodes as shown in FIG. 1 (tetrapolar system). It should be understood that in many applications, the injection of the current and the sensing of voltage may be accomplished with an array of electrodes rather than with two pairs of electrodes as shown herein for simplicity. The appropriate placement of the electrode array, represented herein by the electrodes will be understood by those with skill in the art with reference to the disclosure herein. Suitable placement, for example, is disclosed in U.S. Pat. No. 4,450,527 which is incorporated herein by reference in its entirety.

Figure 2:
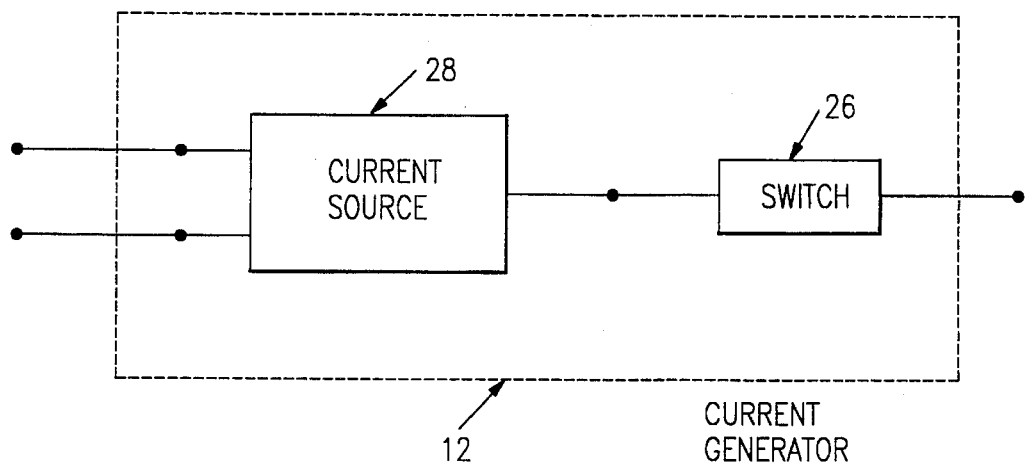
FIG. 2 is a block diagram of an embodiment of a current generator portion of the system illustrated in FIG. 1, according to one aspect of the present invention.

Referring now to FIG. 2, is a block diagram of an embodiment of a current generator 12 portion of the system illustrated in FIG. 1, according to one aspect of the present invention. As illustrated, the current generator comprises a current source 28 for generating a high frequency current output. The current source 28 is coupled across the output terminals of the current generator. In a preferred embodiment, the current source generates a high frequency current with a magnitude ranging between about 1 mA to about 4 mA Root Mean Square (RMS). Also in a preferred embodiment, the signal equivalent frequency is between about 20 kHz (1 cycle period of 50 μsec) and about 100 kHz (period of 10 μsec).

The voltage signal developed across a body segment depends on the impedance of the body segment. For example, for a human thorax with a base impedance of about 30 Ohm, the output current develops a voltage signal between about 30 mV and about 120 mV across the thorax.

The amplitude of the voltage signal is modulated by changes in conductivity in the body segment. In the thorax, such changes are due to changes in the volume of blood within the thorax and by orientation of erythrocytes as a function of blood flow velocity in major arteries. The voltage signal modulation envelope is a superimposed sum of conductivity changes caused by changes in posture, respiration, cardiac cycle and motion artifacts.

A controller for a system for measuring bioimpedance, according to one aspect of the present invention, can comprise an electronic timing circuit coupled to the output terminal of the controller, for generating a periodic control output signal. In a preferred embodiment, only one high frequency cycle current is periodically generated by the current generator. Examples are a one cycle sine wave 30 or a one cycle square wave 32 such as are shown in FIGS. 3a, 3b, 3c and 3d. The period of the control signal is preferably between about 2.5 milliseconds (400 Hz) and about 5 milliseconds (200 Hz).

Figure 3A:
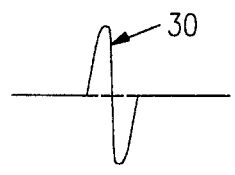
FIGS. 3a and 3b are graphs of a one cycle sine wave and a one cycle square wave, respectively, of a high frequency current output generated by a current generator as illustrated in FIG. 2, according to one aspect of the present invention.
Figure 3B:
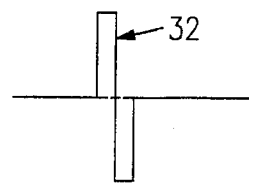
Figure 3C:
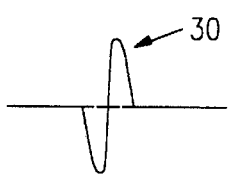
FIGS. 3c and 3d are graphs of a one cycle sine wave and a one cycle square wave, respectively, of a high frequency current output generated by a current generator as illustrated in FIG. 2, according to one aspect of the present invention.
Figure 3D:
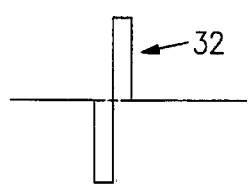
Figure 3E:
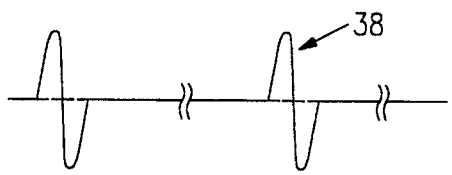
FIGS. 3e and 3f are graphs of multiple cycles of sine wave and square wave signals of high a frequency current output generated by the current generator as illustrated in FIG. 2, according to one aspect of the present invention.
Figure 3F:
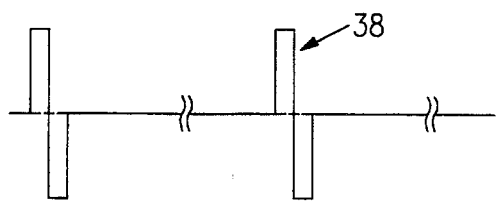
Figure 3G:
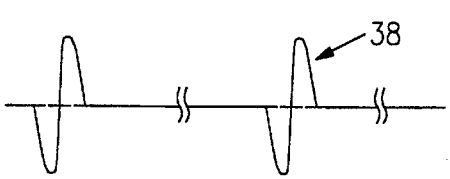
FIGS. 3g and 3h are graphs of multiple cycles of sine wave and square wave signals of high a frequency current output generated by the current generator as illustrated in FIG. 2, according to one aspect of the present invention.
Figure 3H:
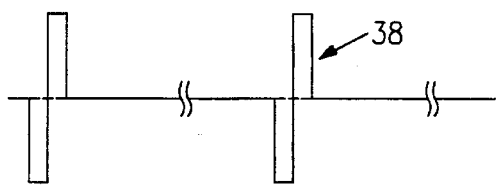
Figure 3I:
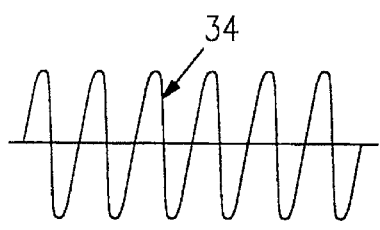
FIGS. 3i and 3j are graphs of sine wave and square wave signals, respectively, of current generators of existing systems for measuring bioimpedance.
Figure 3J:
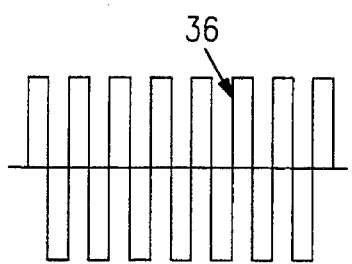
Figure 3K:
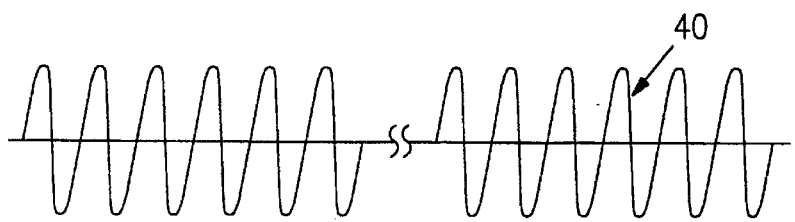
FIGS. 3k and 3l are graphs of bursts of sine wave and square wave cycles of a high frequency current output generated by the current generator as illustrated in FIG. 2, according to one aspect of the present invention.
Figure 3L:
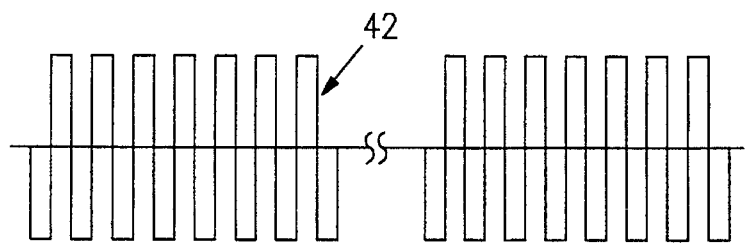

Therefore, compared to continuous sinusoidal 34 or square wave 36 measurement currents generated by current generators of existing systems as shown in FIGS. 3i and 3j, the current 38 generator of the system according to one aspect of the present invention advantageously generates measurement current only periodically as depicted in FIGS. 3e–3h. Further, as exemplified in FIGS. 3k and 3l, bursts of multiple cycles of sine or square wave current output, as opposed to one cycles waves shown in FIGS. 3e–3f, followed by periods of silence, are also contemplated by the present invention. Because of the periodic generation of the output current, the RMS value of the current output is reduced from a milliampere level for existing systems, down to a microampere for the present invention. Accordingly, the present invention provides for a thousand fold reduction in the RMS value of a potentially detrimental measurement current in the body tissue.

The timing circuit of a controller for a system according to the present invention can be a programmable digital counter or timer in which the control signal period can be programmed as appropriate. The timing circuit can also be a subcomponent of a microprocessor system programmed to periodically generate an output signal. Such a subcomponent of a microprocessor is described in the Example I, below.

Referring now to FIG. 4, there is illustrated a block diagram of components of a system for measuring bioimpedance, according to another aspect of the present invention, connected to a human or animal body. As can be seen, the bioimpedance detector 22 further comprises a sensing circuit 44, coupled to the input terminals of the bioimpedance detector. The sensing circuit receives the voltage signal developed across the body segment, and generates an output signal having a magnitude that changes in accordance with the fluid contents or fluid flow in the body segment between the first and the second body portions.

Preferably, the sensing circuit comprises an amplifier 46, coupled to the input terminals of the bioimpedance detector. The amplifier receives and amplifies the voltage signal. The sensing circuit further preferably comprises an analog-to-digital converter 48, responsive to the amplifier, for converting the amplified voltage signal to a digital output signal representative of impedance in the human's body between the first and the second portions. Preferably, the analog-to-digital converter is at least 12 bit (4096 states) in order to enable digital processing of base impedance, impedance change, the of change of impedance over time and the rate of change of impedance over time.

The sensing circuit of the bioimpedance detector can further comprise a digital differentiator 50, responsive to the output signal of the analog-to-digital converter, for generating data representing a differentiated voltage output signal having a magnitude proportional to the rate of change of electrical bioimpedance in the human's body between the first and the second body portions. By using digital processing for differentiation to obtain the rate of change of bioimpedance, the present invention eliminates the need for complex and costly multi-amplifier conventional systems.

The bioimpedance signal and the differentiated voltage signal can be provided as input to a signal processing circuit that analyzes one or both of the signals and determines cardiac parameters that correspond to changes in the electrical bioimpedance signal. The calculated parameters can be communicated to an operator by a visual display such as, for example, a video monitor or a printer.

Referring now to FIG. 5a there is illustrated a graph of a voltage wave form 52 generated by the amplifier portion of a system for measuring bioimpedance, according to one aspect of the present invention. Referring now to FIG. 5b there is illustrated a graph of the differentiated wave form 54 of the graph of FIG. 5a, generated by a digital differentiator portion of a system for measuring bioimpedance, according to one aspect of the present invention.

Operation of the exemplary bioimpedance detectors according to aspects of the present invention, shown in of FIGS. 1 and 4 can be understood by referring to FIGS. 5a and 5b which illustrate wave forms of exemplary electrical bioimpedance signals. FIG. 5a shows a typical voltage wave form generated by the amplifier in FIG. 4 caused by cardiovascular activity. The changes in the amplitude of the voltage generated by the amplifier correspond to changes in the electrical bioimpedance of the body segment caused by changes in the volume of blood in the segment during the cardiac cycle labeled as Z(t) in FIG. 5a. It should be understood that the wave form in FIG. 5a does not include the high frequency components of the detected voltage because such components are filtered out by use of a conventional low-pass filter (not shown). FIG. 5b shows a signal representative of the output of the digital differentiator as dZ/dt. The signal shown in FIG. 5b is the derivative of the electrical bioimpedance signal shown in FIG. 5a.

Referring again to FIG. 4, the sensing circuit of the bioimpedance detector can further comprise a delay circuit 56, connected in series between the amplifier 46 and the analog-to-digital converter 48. The delay circuit samples and holds the output signal of the amplifier for later retrieval by the analog-to-digital converter. The sample and hold circuit extends the duration of the detected voltage for adequate and accurate reading by the analog-to-digital converter.

Referring now to FIG. 6, there is illustrated a block diagram of a system for measuring bioimpedance, according to one aspect of the present invention, where operation of the current generator portion and the bioimpedance detector portion are synchronized by a controller 18 portion. As illustrated, the bioimpedance detector can further comprise a third input terminal 58 electrically connected to the output terminal of the controller, whereby the output signal of the controller is simultaneously received by both the current generator and the bioimpedance detector.

The bioimpedance detector further comprises a synchronizer 60 coupled to the sensing circuit of the bioimpedance detector. The synchronizer 60 controls the operation of the sensing circuit in response to a periodic control signal from the controller 18. As such, the sensing circuit periodically detects the voltage signal across the body segment in synchrony with operation of the current generator.

In operation, the control signal from the controller causes the current generator to generate a one high frequency cycle current, while simultaneously the controller causes the sensing circuit to detect a voltage signal across the body segment and generate an output signal representative of bioimpedance in the body segment. Therefore, the bioimpedance detector operates in the same cycle as the current generator 12. The synchronous operation of the bioimpedance detector with the operation of the current generator ensures that the bioimpedance detector only operates when the current from the current generator has established a voltage signal across the body segment. This synchronization, therefore, advantageously increases the accuracy of the bioimpedance detection.

In a preferred embodiment, the synchronizer comprises an electrically controlled switch responsive to control signals from the controller. To achieve synchronization, the current generator's switch and the bioimpedance's switch open and close at the same time in response to the control signal from the controller.

Referring again to FIG. 4, the sensing circuit 56 of the synchronized bioimpedance detector can further comprise a delay circuit connected in series between the amplifier and the analog-to-digital converter. The delay circuit 56 samples and holds the output signal of the amplifier for later retrieval by the analog-to-digital converter. The delay circuit is preferably used when the speed of the analog-to-digital converter does not allow reading of the detected voltage signal within the same cycle as that of the current generator periodic signal.

According to one aspect of the present invention, there is provided a method for determining or measuring fluid content or fluid flow in a body segment of a human or animal. The method comprises periodically generating a high frequency current, applying the current to a first and a second portion of the body segment, detecting a voltage signal between the first and the second portion caused by impedance to the current flow in the body segment between the first and the second portions, and generating an output signal based on the detected voltage. The output signal is indicative of impedance in the body segment between the first and the second portions.

In one preferred embodiment, the step of detecting further comprises receiving and amplifying the voltage signal, and converting the amplified signal to a digital signal representative of impedance in the body segment. In another preferred embodiment, the step of detection further comprises digitally differentiating the digital signal to generate a differentiated voltage output signal having a magnitude proportional to the rate of change of electrical bioimpedance in the body segment. The method of the present invention also contemplates detecting the voltage signal in synchrony with the periodic generation of the high frequency current.

EXAMPLE I

Referring now to FIG. 7, there is illustrated a block diagram of an example embodiment of a system for measuring bioimpedance, according to one aspect of the present invention, connected to a human body. The system comprises a synchronous current generator with a pair of surface, pre-jelled, electrodes marked A and D connected to the thorax of a human body as shown. The system further comprises a high frequency amplifier having two input terminals connected to the thorax via electrodes B and C as shown.

The system further comprises a 12 bit, or higher, analog-to-digital converter, and a microprocessor connected to the output of the A/D convertor. The system can optionally comprise a sample and hold circuit connected in series between the high frequency amplifier and the analog-to-digital converter.

In operation, the microprocessor generates periodic pulses denoted as M and N in FIG. 7, where the M pulse is connected to both the current generator and the sample and hold circuit, and the N pulse is connected to both the current generator and the analog-to-digital converter. The M and N pulses cause the current generator to periodically generate a one high frequency (HF) cycle current, that is a one cycle sign wave or one cycle square wave. The current generates a voltage, or thoracic electrical bioimpedance (TEB), signal.

During the N (positive) half of the one HF cycle, the TEB signal generated is simultaneously detected by the analog-to-digital converter. Therefore, the reading of the HF voltage signal developed across the thorax during the N half of the HF cycle is simultaneously and synchronously performed by the analog-to-digital converter. The M (negative) half of the one HF cycle is only used to eliminate a potential for the DC offset or for a DC current component flowing through body. It can also be used to discharge the sample and hold circuit from the previous cycle.

To achieve adequate TEB signal resolution, the analog-to-digital converter must be more than 12 bit (4096 states)

to enable digital processing of impedance ($Z_o$), changes in impedance ($\Delta Z$), and rate of change of impedance ($dZ/dt$) with one analog-to-digital converter. Functions such as differentiation ($dZ/dt$), are performed digitally by the microprocessor. In case the speed of the analog-to-digital converter does not allow reading the N part of the detected TEB signal within the one-half of the HF cycle (in 25 μsec. for 20 kHz or in 5 μsec. for 100 kHz), the sample (S&H) circuit extends the duration of the detected TEB signal for subsequent adequate and accurate reading by the analog-to-digital converter. Since the one HF cycle measurement current in the present invention is repeated only at the sampling frequency of the analog-to-digital converter, i.e., every 2.5 or every 5 milliseconds (400 or 200 times per second), the corresponding reduction in the RMS value of the measurement current is reduced from a milliampere in existing systems down to a microampere level in the present invention.

Figure 8:
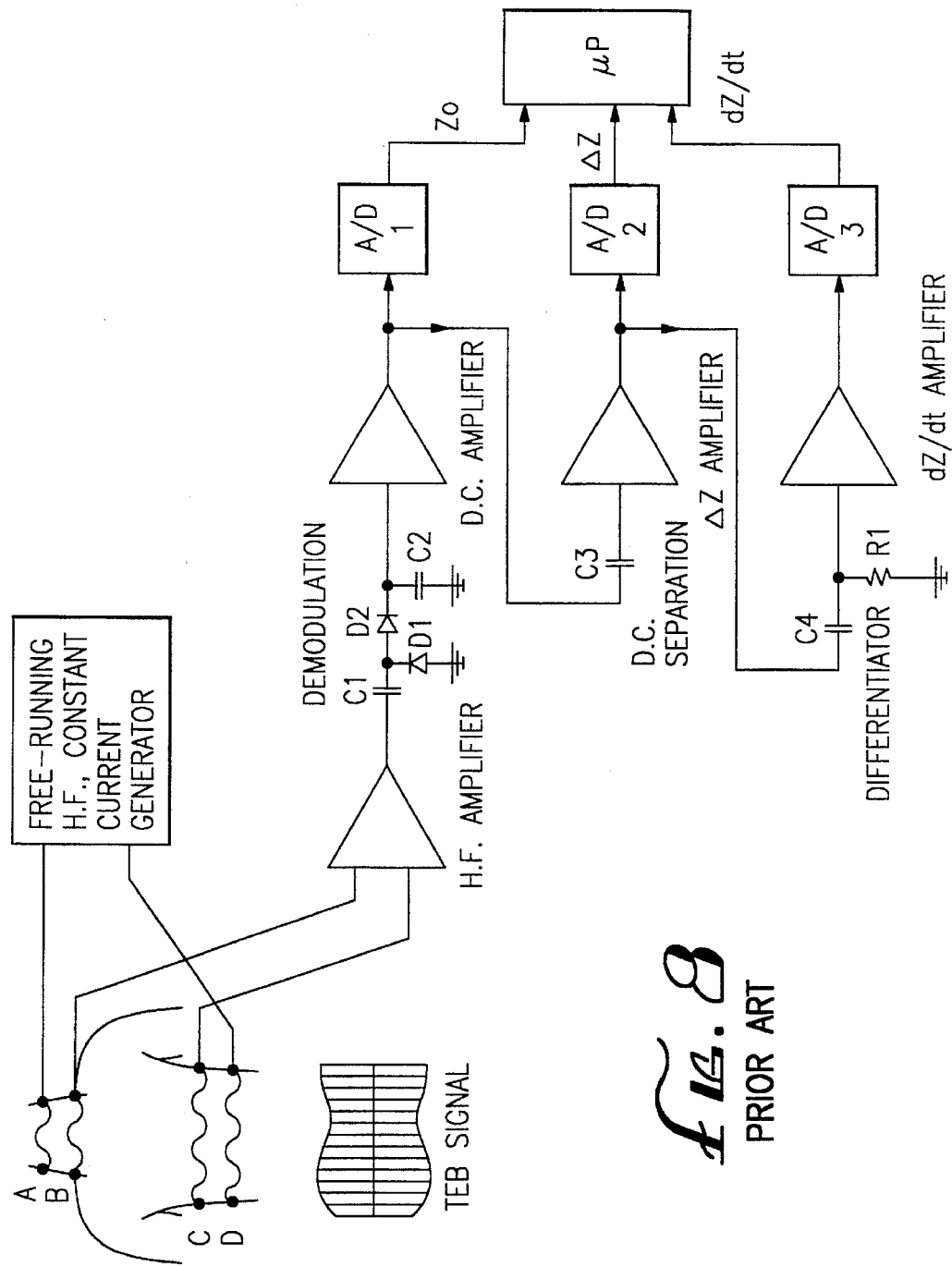
FIG. 8 is a block diagram illustrating an example of an existing system for measuring bioimpedance connected to a human body.

Additionally, use of digital processing eliminates the need for multi-level amplifier circuits of existing systems, such as the system illustrated in FIG. 8. In such an existing system, the TEB signal is first amplified by a first amplifier (HF amplifier), and the HF component of the amplified signal is demodulated utilizing a peak detector circuit utilizing diodes D1 and D2, and capacitors C1 and C2 interconnected as shown. The modulated signal is then amplified by a second amplifier (DC amplifier) and digitized by a first analog-to-digital (A/D) converter to obtain a digital value for the base impedance $Z_o$. The $Z_o$ signal is then provided to a microprocessor. A capacitor C3 removes the DC component of the TEB signal, generating an impedance change signal $\Delta Z$ which is in turn amplified by a second amplifier and digitized using a second A/D converter and provided to the microprocessor. The amplified $\Delta Z$ signal is further differentiated by another resistive-capacitive circuit utilizing a capacitor C3 and a resistor R1 interconnected as shown. The differentiated signal, $dZ/dt$, is amplified by a third amplifier and then digitized by a third A/D converter and provided to the microprocessor.

The complexity of existing systems, as shown in FIG. 8, requires consecutive levels of amplification (HF, DC, AZ, and $dZ/dt$), where each amplification level amplifies the input noise from the HF amplifier, requiring an increase in the magnitude of the measurement current to improve signal to noise ratio. The system requires numerous circuits (amplifiers, A/D converters, ...) which increase area of the printed circuit board, decrease reliability, and increase cost and power consumption.

By contrast, the example embodiment of the present invention utilizes only one amplifier and one analog to digital converter. All differentiation and processing functions are performed digitally by the microprocessor. Therefore, the system according to one aspect of the present invention advantageously reduces circuit complexity, improves signal to noise ratio, reduces the number of circuits needed, reduces the printed circuit board area needed, and reduces manufacturing and power consumption costs. In addition, the system has increased reliability.

Although the example above has been described in conjunction with electrical bioimpedance detection for the thorax (TEB), the same system and method are applicable for any electrical bioimpedance application on other segments of the body, including superficial organs.

The above discussion of the bioimpedance detection system shown in FIG. 7 is one possible example of the operation of the system according to one aspect of the present invention. It is to be understood that the invention is not limited to operation in accordance with the system shown in FIG. 7, and that one with skill in the art would readily understand how to modify the disclosed system to obtain equivalent results without departing from the spirit and scope of the present invention.

What is claimed is:

1. A system for determining or measuring fluid content or fluid flow in a human or animal body segment, comprising:
    (a) a current generator means for generating a periodic high frequency current output in response to a periodic control signal, the current generator means comprising:
        (i) a first and a second output terminal for carrying the current output, wherein the first and the second output terminal means are adapted to be electrically connectable to a first and a second portion of the human or animal body segment, respectively; and
        (ii) an input terminal means for receiving the control signal;
    (b) a controller means for generating the periodic control signal to control operation of the current generator means, the controller means including an output terminal for carrying the control signal, wherein the output terminal of the controller means is electrically connected to the input terminal means of the current generator means; and
    (c) an electrical bioimpedance detector means for detecting a voltage between the first and the second portion of the human or animal body segment caused by the current output of the current generator means flowing between the first and the second portion of the human or animal body segment, and for generating an output signal in response, wherein the output signal is indicative of impedance in the human or animal body segment between the first and the second portion, the bioimpedance detector means comprising:
        (i) a first and a second input terminal means for detecting said voltage, wherein the first and the second input terminal means of the bioimpedance detector means are adapted to be electrically connectable to the human or animal body segment proximate the first and second output terminal means of the current generator means, respectively; and
        (ii) an output terminal means for carrying the detector's output signal.

2. The system of claim 1 wherein the bioimpedance detector means further comprises a sensing circuit means, coupled to the input terminal means of the bioimpedance detector means, for receiving said voltage and generating an output signal having a magnitude that changes in accordance with the content or flow of fluids in the human or animal body segment between the first and second body segment portions.

3. The system of claim 2 wherein the bioimpedance detector further comprises:
    (a) a third input terminal means electrically connected to the output terminal means of the controller means, whereby the central signal of the controller means is simultaneously received by both the current generator means and the bioimpedance detector means; and
    (b) a synchronizer means, coupled to the sensing circuit means, for controlling the operation of the sensing circuit means in response to the control signal from the controller means, whereby the sensing circuit means periodically detects said voltage in synchrony with the operation of the current generator means.

4. The system of claim 3 wherein the synchronizer means comprises an electrically controlled switch responsive to the control signal from the controller means.

5. The system of claim 2 wherein the sensing circuit means comprises:
   (a) an amplifier means, coupled to the input terminal means of the bioimpedance detector means, for receiving and amplifying said voltage as an output signal; and
   (b) an analog-to-digital converter means, responsive to the output signal of the amplifier means, for converting the output signal to a digital output signal representative of impedance in the human or animal body segment between the first and the second portions.

6. The system of claim 5 wherein the sensing circuit means further comprises a digital differentiator means, responsive to the digital output signal of the analog-to-digital converter means, for generating data representing a differentiated voltage output signal having a magnitude proportional to a rate of change of electrical bioimpedance in the human or animal body segment between the first and the second portions.

7. The system of claim 5 wherein the sensing circuit means further comprises a processor means, responsive to the digital output signal of the analog-to-digital converter means, for processing data.

8. The system of claim 5 wherein the bioimpedance detector means further comprises a delay circuit means, connected in series between the amplifier means and the analog-to-digital converter means, for sampling and holding the output signal of the amplifier means for later retrieval by the analog-to-digital converter means.

9. The system of claim 1 wherein the current generator means further comprises:
   (a) a current source means for generating a high frequency current output, the current source means being coupled across the output terminal means of the current generator means; and
   (b) an electrically controlled switch coupled to the current source means, for regulating the operation of the current source means in response to the control signal from the controller means, whereby the current source means generates the high frequency current output only when the switch is closed.

10. The system of claim 1 wherein the controller means further comprises a timing circuit means, coupled to the output terminal of the controller means, for generating the periodic control signal.

11. The system of claim 10 wherein the timing circuit means is a microprocessor.

12. A method of determining or measuring fluid content or fluid flow in a human or animal body segment, comprising:
   (a) periodically generating a high frequency current;
   (b) applying the current to a first and a second portion of the human or animal body segment;
   (c) detecting a voltage between a third and a fourth portion of the human or animal body segment, wherein the third and the fourth portions are located proximate the first and the second portion of the human or animal body segment, and the detected voltage is caused by impedance to the current flow in the human or animal body segment between the third and the fourth portions; and
   (d) generating a signal based on the detected voltage, wherein the signal is indicative of impedance in the human or animal body segment between the third and the fourth portions.

13. The method of claim 12 wherein the step of detecting further comprises:
   (a) receiving and amplifying said voltage to generate an amplified signal; and
   (b) converting the amplified signal to a digital signal representative of impedance in the human or animal body segment between the third and the fourth portions.

14. The method of claim 13 further comprising the step of digitally differentiating the digital signal to generate a differentiated voltage output signal having a magnitude proportional to a rate of change of electrical bioimpedance in the human or animal body segment between the third and the fourth portions 15. The method of claim 12 wherein the step of detecting comprises periodically detecting said voltage in synchrony with the periodic generation of the current.

16. The method of claim 12 wherein the step of detecting further comprises sampling and holding the output signal of the amplifier for later retrieval and conversion to a digital signal.

* * * * *